(12) United States Patent
Kung Farber et al.

(10) Patent No.: US 6,797,672 B2
(45) Date of Patent: Sep. 28, 2004

(54) FUNGICIDAL COMPOSITIONS BASED ON FLUDIOXONIL

(75) Inventors: Ruth Beatrice Kung Farber, Basel (CH); Gertrude Knauf-Beiter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 1 day.

(21) Appl. No.: 10/312,111

(22) PCT Filed: Jul. 2, 2001

(86) PCT No.: PCT/EP01/07528

§ 371 (c)(1),
(2), (4) Date: Apr. 25, 2003

(87) PCT Pub. No.: WO02/01955

PCT Pub. Date: Jan. 10, 2002

(65) Prior Publication Data

US 2003/0166695 A1 Sep. 4, 2003

(51) Int. Cl.⁷ .......................... A01N 43/36; A01N 43/50
(52) U.S. Cl. ...................................... 504/138; 504/139
(58) Field of Search .................................. 504/138, 139

(56) References Cited

FOREIGN PATENT DOCUMENTS

WO          9927789         *   6/1999

* cited by examiner

*Primary Examiner*—Alton N. Pryor
(74) *Attorney, Agent, or Firm*—William A. Teoli, Jr.

(57) ABSTRACT

Novel fungicidal compositions for the treatment of phytopathogenic diseases of crop plants and against infestation on propagation stock of plants or on other vegetable material, especially phytopathogenic fungi, and to a method of combating phytopathogenic diseases on crop plants or in post-harvest storage and for seed dressing. The invention relates in particular to the control or prevention of diseases in the post-harvest storage period of harvested fruits. It has now been found that the use of a) 4-(2,2-difluoro-1,3-benzodioxol-7-yl)pyrrole-3-carbonitrile ("fludioxonil") (The Pesticide Manual, 11th. edition, 1997, 334), component I in association with b) either 2-(thiazol-4-yl)benzimidazol, component IIA ("thiabendazole") (The Pesticide Manual, 11th. edition, 1997, 701); or 1-(β-allyloxy-2,4-dichlorophenylethyl)imidazole, component IIB ("imizalil") (The Pesticide Manual, 11th. edition, 1997, 410) is particularly effective in combating or preventing fungal diseases of crop plants. These combinations exhibit synergistic fungicidal activity.

13 Claims, No Drawings

FUNGICIDAL COMPOSITIONS BASED ON FLUDIOXONIL

This appl. is a 371 of PCT/EP01/07528 filed Jul. 2, 2001.

The present invention relates to novel fungicidal compositions for the treatment of phytopathogenic diseases of crop plants and against infestation on propagation stock of plants or on other vegetable material, especially phytopathogenic fungi, and to a method of combating phytopathogenic diseases on crop plants or in post-harvest storage and for seed dressing.

The invention relates in particular to the control or prevention of diseases in the post-harvest storage period of harvested fruits.

It has now been found that the use of
a) 4-(2,2-difluoro-1,3-benzodioxol-7-yl)pyrrole-3-carbonitrile ("fludioxonil") (The Pesticide Manual, 11th. edition, 1997, 334), component I in association with
b) either 2-(thiazol-4-yl)benzimidazol, component IIA ("thiabendazole") (The Pesticide Manual, 11th. edition, 1997, 701); or
1-(β-allyloxy-2,4-dichlorophenylethyl)imidazole, component IIB ("imazalil") (The Pesticide Manual, 11th. edition, 1997, 410)
is particularly effective in combating or preventing fungal diseases of crop plants. These combinations exhibit synergistic fungicidal activity.

Favorable mixture ratios of the two active ingredients are I:II=20:1 to 1:20, preferably I:II=10:1 to 1:10 and 5:1 to 1:5.

The active ingredient combinations I+II according to the invention have very advantageous properties in the protection of plants and during post-harvest storage of fruits against the outbreak of disease.

The active ingredient combinations are effective against phytopathogenic fungi belonging to the following classes: Ascomycetes (e.g. Venturia, Podosphaera, Erysiphe, Monilinia, Sclerotinia, Mycosphaerella, Uncinula); Basidiomycetes (e.g. the genus Hemileia, Rhizoctonia, Tilletia, Puccinia); Fungi imperfecti (e.g. Botrytis, Helminthosporium, Rhynchosporium, Fusarium, Septoria, Cercospora, Alternaria, Penicillium spp., Pyricularia and *Pseudocercosporella herpotrichoides*).

With the present active ingredient compositions, the microorganisms appearing on plants or plant parts (fruits, flower, foliage, stems, tubers, roots) of different useful plants can be stopped or destroyed, whereby plant parts growing later also remain free from such microorganisms. They may also be used as post-harvest application or as dressing, or the treatment of plant propagation material, specially seeds.

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers) and their seeds. This list does not represent any limitation.

The combinations of the present invention may also be used in the area of protecting technical material against attack of fungi. Technical areas include wood, paper, leather, constructions, cooling and heating systems, ventilation and air conditioning systems, and the like. The combinations according the present invention can prevent the disadvantageous effects such as decay, discoloration or mold.

Throughout this document the expression combination stands for the various combinations of the components I and II, e.g. in a single "ready-mix" form, in a combined spray mixture composed from separate formulations of the single active ingredient components, e.g. a "tank-mix", and in a combined use of the single active ingredients when applied in a sequential manner, i.e. one after the other with a reasonable short period, e.g. a few hours or days. The order of applying the components I and II is not essential for working the present invention.

The combinations according to the present invention are particularly effective against Botrytis spp., Fusarium spp. and Penicillium spp., in particular against pathogens of fruits plants such as citrus, pomes, stone fruits and soft fruits and bananas as well as potatoes and the corresponding fruits during post-harvest storage.

The amount of combination of the invention to be applied, will depend on various factors such as the compound employed, the subject of the treatment (plant, soil, post-harvest, seed), the type of treatment (e.g. spraying, dusting, seed dressing), the purpose of the treatment (prophylactic or therapeutic), the type of fungi to be treated and the application time.

It has been found that the use of compounds IIA and IIB in combination with the compound of formula I surprisingly and substantially enhance the effectiveness of the latter against fungi, and vice versa. Additionally, the method of the invention is effective against a wider spectrum of such fungi that can be combated with the active ingredients of this method, when used solely.

The invention also relates to a method of controlling fungi, which comprises treating a site, for example a plant, its locus of growth, or during post-harvest storage of fruits, that is infested or liable to be infested by fungi with the active component I and with the active component II in any desired order or simultaneously.

The weight ratio of I:II is so selected as to give a synergistic fungicidal action. The synergistic action of the composition is apparent from the fact that the fungicidal action of the composition of I+II is greater than the sum of the fungicidal actions of I and II.

The method of the invention comprises applying to the plants to be treated or the locus thereof in admixture or separately, a fungicidally effective aggregate amount of a compound I and a compound of component b).

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, germinated or soaked seeds.

The combinations are applied by treating the fungi or the seeds, plants or materials threatened by fungus attack, or the soil with a fungicidally effective amount of the active ingredients.

The novel combinations are extremely effective against phytopathogenic fungi. Some of the have a systemic action and can be used as foliar and soil fungicides, for post-harvest fruits during storage and for seed dressing.

The agents may be applied before or after infection of the materials, plants, during post-harvest storage of fruits or seeds by the fungi.

When applied to the plants or the post-harvest fruits the compound of formula I is applied at a rate of 10 to 150 g/100 l, particularly 20 to 100 g/100 l, e.g. 20, 50, or 100 g/100 l, in association with 10 to 1000 g/100 l, particularly 30 to 600 g/100 l, e.g. 30 g/100 l, 40 g/100 l, 75 g/100 l, 80 g/100 l, 100 g/100 l, 125 g/100 l, 150 g/100 l, 175 g/100 l, 200 g/100 l, 300 g/100 l, 500 g/100 l, depending on the class of chemical employed as component b). Where the component b) is compound IIA for example 50 to 200 g a.i./100 l is applied in association with the compound of formula I. Where the component b) is compound IIB for example 25 to 200 g a.i./100 l is applied in association with the compound of formula I. In agricultural practice the application rates of the combination depend on the type of effect desired, and range from 5 to 1000 g of active ingredient per 100 l.

When the active ingredients are used for treating seed, rates of 0.001 to 50 g a.i. per kg, and preferably from 0.01 to 10 g per kg of seed are generally sufficient.

The invention also provides fungicidal compositions comprising a compound of formula I and a compound of component b).

The composition of the invention may be employed in any conventional form, for example in the form of a twin pack, an instant granulate, a flowable or a wettable powder in combination with agriculturally acceptable adjuvants. Such compositions may be produced in conventional manner, e.g. by mixing the active ingredients with appropriate adjuvants (diluents or solvents and optionally other formulating ingredients such as surfactants).

The term diluent as used herein means any liquid or solid agriculturally acceptable material including carriers which may be added to the active constituents to bring them in an easier or improved applicable form, respectively, to a usable or desirable strength of activity. Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water. The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable non-absorbent carriers are, for example, calcite or sand. In addition, a great number of materials of inorganic or organic nature can be used, e.g. especially dolomite or pulverized plant residues. Depending upon the nature of the compounds of formula I and component b) to be formulated, suitable surface-active compounds are non-ionic, cationic and/or anionic surfactants having good emulsifying, dispersing and wetting properties. The term "surfactants" will also be understood as comprising mixtures of surfactants. Particularly advantageous application-promoting adjuvants are also natural or synthetic phospholipids of the cephalin and lecithin series, e.g. phosphatidylethanolamine, phosphatidylserine, phosphatidylglycerol and lysolecithin.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid adjuvant(s), the active agent consisting of at least the compound of formula I together with a compound of component b), and optionally other active agents, particularly microbicides or conservatives or the like. Concentrate forms of compositions generally contain in between about 2 and 80%, preferably between about 5 and 70% by weight of active agent. Application forms of formulation may for example contain from 0.01 to 20% by weight, preferably from 0.01 to 5% by weight of active agent.

The Examples which follow serve to illustrate the invention, "active ingredient" denoting a mixture of compound I and a compound of component b) in a specific mixing ratio.

Formulations may be prepared analogously to those described in, for example, WO 97/33890.

Slow Release Capsule Suspension 28 parts of a combination of the component I and a compound of component b), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and
51.6 parts of water until the desired particle size is achieved. To this emulsion a mixture of 2.8 parts
1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8–15 microns.

The resulting formulation is applied to seeds as an aqueous suspension in an apparatus suitable for that purpose.

Seed Dressing Formulation 25 parts of a combination of components I and II, 15 parts of dialkylphenoxypoly(ethylenoxy)ethanol, 15 parts of fine silica, 44 parts of fine kaolin, 0.5 parts of Rhodamine B as a colorant and 0.5 parts of Xanthan Gum are mixed and ground in a contraplex mill at approx. 10000 rpm to an average particle size of below 20 microns. The resulting formulation is applied to the seeds as an aqueous suspension in an apparatus suitable for that purpose.

Whereas commercial products will preferably be formulated as concentrates, the end user will normally employ dilute formulations.

Biological Examples

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20–22; 1967):

ppm=milligrams of active ingredient (=a.i.) per litre of spray mixture

X=% action by active ingredient I using p ppm of active ingredient

Y=% action by active ingredient II using q ppm of active ingredient.

According to Colby, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

Alternatively the synergistic action may also be determined from the dose response curves according to the so-called WADLEY method. With this method the efficacy of the a.i. is determined by comparing the degree of fungal attack on treated plants with that on untreated, similarly inoculated and incubated check plants. Each a.i. is tested at 4 to 5 concentrations. The dose response curves are used to establish the EC90 (i.e. concentration of a.i. providing 90% disease control) of the single compounds as well as of the combinations (EC $90_{observed}$) The thus experimentally found values of the mixtures at a given weight ratio are compared with the values that would have been found were only a complementary efficacy of the components was present (EC 90 (A+B)$_{expected}$). The EC90 (A+B)$_{expected}$ is calculated according to Wadley (Levi et al., EPPO-Bulletin 16, 1986, 651–657):

$$EC90\,(A+B)_{expected} = \frac{a+b}{\frac{a}{EC90\,(A)_{observed}} + \frac{b}{EC90\,(B)_{observed}}}$$

wherein a and b are the weight ratios of the compounds A and B in the mixture and the indexes (A), (B), (A+B) refer to the observed EC 90 values of the compounds A, B or the given combination A+B thereof. The ratio EC90 (A+B)$_{expected}$/EC90 (A+B)$_{observed}$ expresses the factor of interaction (F). In case of synergism, F is >1.

EXAMPLE B-1

Efficacy Against *Botrytis cinerea* on Apple

In an apple fruit cv. Golden Delicious 3 holes were drilled and each filled with 50 µl droplets of the formulated test composition. Two hours after application 50 µl of a spore suspension of *B. cinerea* (4×10$^5$ conidia/ml) were pipetted on the application sites. After an incubation period of 5 days at 20° C. in a growth chamber the % infected fruit area was determined. The activity was calculated relative to the disease rate on untreated apple fruits. The fungicide interactions in the mixture were calculated according to Colby.

Results

TABLE 1

| Fludioxonil mg a.i./l | Thiabendazole mg a.i./l | Ratio | % activity observed | % activity expected | SF Colby |
|---|---|---|---|---|---|
| 5 | | | 67 | | |
| 2.5 | | | 54 | | |
| 0.1 | | | 2 | | |
| | 25 | | 5 | | |
| | 5 | | 12 | | |
| | 2.5 | | 10 | | |
| | 1 | | 10 | | |
| | 0.5 | | 5 | | |
| 2.5 | 25 | 1:10 | 67 | 56 | 1.2 |
| 0.1 | 1 | 1:10 | 17 | 12 | 1.4 |
| 0.1 | 0.5 | 1:5 | 16 | 7 | 2.3 |
| 2.5 | 5 | 1:2 | 73 | 59 | 1.2 |
| 5 | 5 | 1:1 | 100 | 71 | 1.4 |
| 2.5 | 2.5 | 1:1 | 79 | 58 | 1.3 |

TABLE 2

| Fludioxonil mg a.i./l | Imazalil mg a.i./l | Ratio | % activity observed | % activity expected | SF Colby |
|---|---|---|---|---|---|
| 5 | | | 67 | | |
| 0.5 | | | 24 | | |
| 0.1 | | | 2 | | |
| | 25 | | 21 | | |
| | 5 | | 0 | | |
| | 1 | | 6 | | |
| 0.1 | 1 | 1:10 | 10 | 8 | 1.2 |
| 5 | 25 | 1:5 | 82 | 74 | 1.1 |
| 0.5 | 1 | 1:2 | 33 | 28 | 1.2 |
| 5 | 5 | 1:1 | 87 | 67 | 1.3 |

EXAMPLE B-2

Efficacy Against Fusarium on Wheat

A conidia suspension of Fusarium (7×10$^5$ conidia/ml) is mixed with the formulated test composition. The mixture is applied into a pouch which was previously equipped with a filter paper. After application wheat seeds (cv. Orestis) are sown into then upper fault of the filter paper. The prepared pouches are then incubated for 11 days at approx. 10–18° C. and a relative humidity of 100% with a photo period of 14 hours. The evaluation is made by assessing the degree of disease occurrence in the form of brown lesions on the roots.

EXAMPLE B-3

Efficacy Against Penicillium on Lemon Fruits

Lemon fruits were inoculated by placing 50 µl spore suspension with 0.1% tween 20 and a density of 500000 spores/ml into each hole (two holes/fruit) which are prepared by boring the holes into the lemon peel approximately 1 cm diameter and a depth of 1–1.5 mm. The fruits were stored in covered plastic boxes under light at 20° C. and checked 5–7 days after inoculation.

The mixtures according to the invention exhibit good activity in these examples.

What is claimed is:

1. A method of combating phytopathogenic diseases caused by phytopathogenic fungi, on crop plants or post-harvest fruits which comprises applying to the crop plants or the locus thereof being infested with said phytopathogenic disease an effective amount of a mixture consisting essentially of a) 4-(2,2-difluoro-1,3-benzodioxol-7-yl)pyrrole-3-carbonitrile, component I in association with b) either 2-(thiazol-4-yl)benzimidazol, component IIA; or 1-(β-allyloxy-2,4-dichlorophenylethyl)imidazole, component IIB which synergistically enhances the activity against phytopathogenic diseases.

2. A method according to claim 1, wherein b) compound is the compound IIA.

3. A method according to claim 1, wherein b) compound is the compound IIB.

4. A method according to claim 1, wherein the phytopathogenic fungi belongs to the class of fungi imperfecti.

5. A method according to claim 1, wherein said mixture is applied to post-harvest fruits during post-harvest storage.

6. A method according to claim 1, which comprises applying to the plants, or their locus of growth, or the post-harvest fruits, which are infected or liable to be infected, a) compound I and b) a compound selected from compound IIA and compound IIB in any order or simultaneously.

7. A method according to claim 1, wherein said crop plant is a plant propagation material.

8. A method according to claim 7, wherein the plant propagation material is seed.

9. A fungicidal composition comprising a fungicidally effective combination of a) 4-(2,2-difluoro-1,3-benzodioxol-7-yl)pyrrole-3-carbonitrile, component I in association with b) either 2-(thiazol-4-yl)benzimidazol, component IIA; or 1-(β-allyloxy-2,4-dichlorophenylethyl)imidazole, compound IIB, wherein the components are present in amounts which synergistically enhances the activity against phytopathogenic diseases.

10. A composition according to claim 9, wherein the weight ratio of a) to b) is between 20:1 and 1:20.

11. A composition according to claim 9, wherein b) compound is the compound IIA.

12. A composition according to claim 9, wherein b) compound is the compound IIB.

13. A composition according to claim 9, wherein the components a) I and b) II are present in amounts which synergistically enhance the activity against phytopathogenic fungi belonging to the class of fungi imperfecti.

* * * * *